United States Patent [19]
Malick

[11] 3,962,042
[45] June 8, 1976

[54] FERMENTATION APPARATUS

[75] Inventor: Emil A. Malick, Bartlesville, Okla.

[73] Assignee: Phillips Petroleum Company, Bartlesville, Okla.

[22] Filed: Jan. 13, 1975

[21] Appl. No.: 540,562

[52] U.S. Cl. ................................................. 195/143
[51] Int. Cl.² ................................................ C12B 1/16
[58] Field of Search ..................................... 195/143

[56] References Cited
UNITED STATES PATENTS
3,660,244   5/1972   Che ................................... 195/143

*Primary Examiner*—Alvin E. Tanenholtz

[57] ABSTRACT

An apparatus for the culturing of microorganisms in an aerobic fermentation process. The apparatus includes a vessel with a chamber or reaction zone therein. A draft tube with opposite ends is mounted in the chamber and defines a fluid flow path. A pump means is positioned adjacent one of the draft tube ends and induces flow of fluid through the draft tube and a flow path defined by the draft tube and one interior surface of the vessel. An impeller is positioned between the draft tube and the interior surface of the vessel to assist fluid flow along the flow path defined by same.

6 Claims, 2 Drawing Figures

FERMENTATION APPARATUS

In recent years there has been increasing interest in the production of low cost protein by fermentation processes. Such fermentation processes include the culturing of microorganisms on relatively inexpensive substrates such as n-paraffins, natural gas, methanol and the like wherein the processes produce single cell protein (SCP). Protein produced by such processes offers hope for a major new protein source which is independent of agricultural land use. This is important because of the increasing world population and recent shortages in the usual sources of inexpensive protein. Generally, the production of single cell protein is achieved by the culturing of a suitable microorganism in an aerobic fermentation process. Typically, such processes require the presence of a suitable feedstock or substrate to provide a source of carbon and energy for the microorganism growth. In addition, the presence of mineral nutrients in aqueous form is also required. Since the process is an aerobic process, relatively large amounts of oxygen are required for the growth of the microorganism. Usually, the oxygen is supplied by passing air through the fermenter at a rate of approximately 1 to 3 volumes of air per fermenter volume per minute.

For efficient utilization of the microorganism, feedstock, mineral nutrients and the fermenting apparatus, it has been found that high oxygen transfer rates are needed to achieve rapid cell growth. One approach to this problem has been the use of a fermenter which operates essentially at a foam-filled condition and is able to provide the necessary high oxygen transfer rates. High oxygen transfer rate is enhanced by circulation of a fluid medium within the fermenting apparatus by use of suitable stirring or pumping means. Generally speaking, the larger the fermenting apparatus as would be required for commercial utilization of a fermentation process, the more important good circulation becomes.

The principal objects of the present invention are: to provide a fermentation apparatus for culturing of microorganisms in an aerobic fermentation process with the apparatus having flow inducing means for increasing the circulation of fermentation medium; to provide such an apparatus which has a relatively high transfer rate of oxygen which is used in the fermentation process; to provide such an apparatus which has more positive circulation of the fermentation medium; to provide such an apparatus which effects good mixing of the fermentation medium; and to provide such an apparatus which is simple in construction, positive in operation and well adapted for its intended use.

Other objects and advantages of the present invention will become apparent from the following detailed description taken in connection with the accompanying drawings wherein are set forth by way of illustration and example certain embodiments of this invention.

Figure 1:
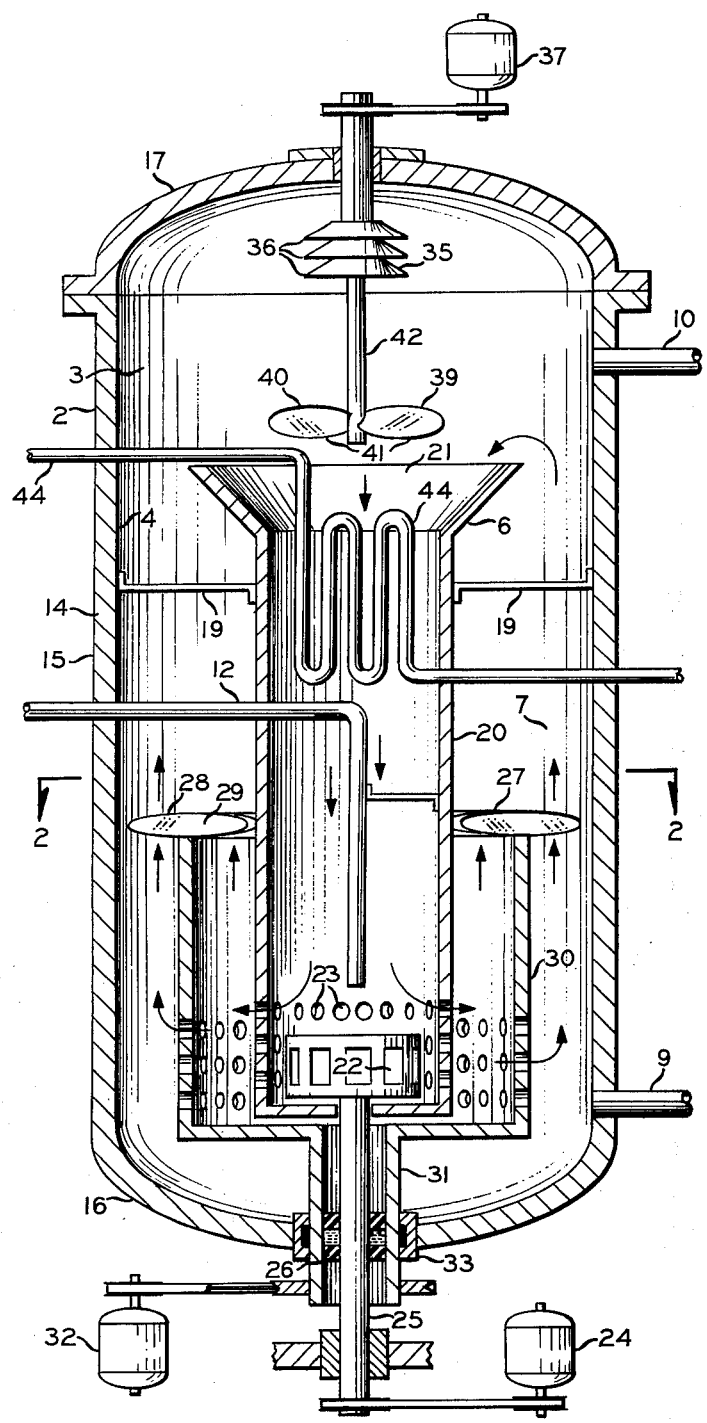
FIG. 1 is a side elevation sectional view of a fermentation apparatus.
Figure 2:
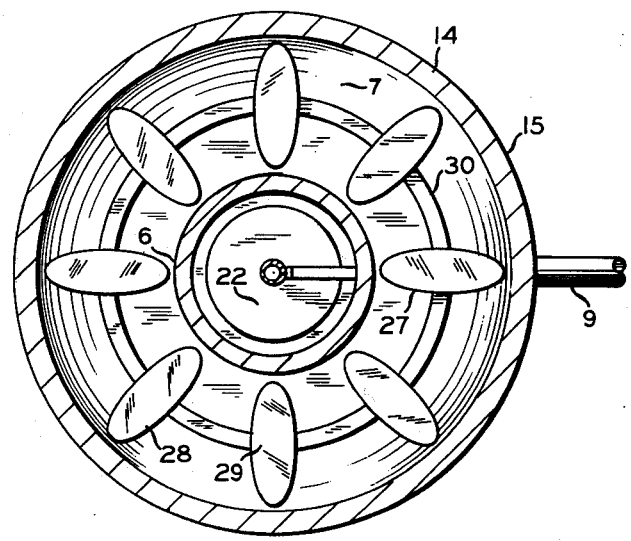
FIG. 2 is a sectional view of the apparatus taken along the line 2—2, FIG. 1.

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting but merely as a basis for the claims and as a representative basis for teaching one skilled in the art to variously employ the present invention in virtually any appropriate detailed structure.

Referring more in detail to the drawings:

The reference numeral 1 designates generally a fermentation apparatus which is comprised of a vessel 2 having a reaction zone or chamber 3 defined partially by an interior surface 4. A draft tube 6 is mounted in the chamber 3 and is spaced from the interior surface 4 forming a flow path 7 therebetween. Feedstock which would typically include a carbonaceous material and mineral nutrients and a source of nitrogen are supplied to the vessel 2 through an inlet 9. Also provided is an outlet 10 for the removal of product which preferably is in the form of a foam taken from an upper portion of the vessel 2. An oxygen supply 12 also communicates with the chamber 3 for supply of oxygen in some form such as air or oxygen-enriched air for dispersion in a fluid medium or ferment.

In the illustrated structure the vessel 2 is of generally standard construction having a shell 14 comprised of a side wall 15 and bottom and top walls 16 and 17, respectively. Preferably, the side wall 15 is generally cylindrical in shape. The vessel 2 is made of a corrosion-resistant and strong and durable material such as stainless steel which is easy to maintain in a sanitary condition. The draft tube 6 is suitably mounted in the chamber 3 as by supports 19 which secure the draft tube 6 in position in the chamber 3. The draft tube 6 preferably has a generally circular cross section having a smaller diameter than the diameter of the chamber 3 and is spaced from the interior surface 4 a distance sufficient to form the flow path 7 between an exterior surface 20 of the draft tube 6 and the interior surface 4 of the side wall 15 whereby the flow path 7 is generally annular in shape.

The draft tube has a flow opening adjacent each end and, as shown, has an upper open end 21 and a bottom end which preferably has pump means 22 adjacent same for inducing flow of fluid downwardly through the draft tube 6. Any suitable pump means can be provided and preferably is of a turbine type. Openings 23 are through the draft tube 6 adjacent the lower end thereof whereby fluid pumped by the pump means 22 is discharged through the openings 23 and preferably the fluid is emulsified by passing through the openings 23. The pump means 22 are power operated such as by a motor 24 such as an electric motor which preferably is speed controllable to control the operating speed of the pump 22. The motor 24 is connected to the pump 22 by a shaft 25 which extends through the bottom wall 16 and is suitably rotatably mounted in a bearing assembly 26 and sealed against leakage.

Flow inducing means 27 are positioned in the flow path 7 to help induce flow of fluid through the flow path 7. Any suitable means can be used and, as shown, an impeller-type of pump or fan is positioned between the exterior surface 20 and the interior surface 4. Preferably, the impeller 28 has a plurality of blades 29 of any suitable shape which are secured to a suitable support 30 which surrounds the exterior of the draft tube 6 and is operably connected to drive means for operation of the impeller 28. The blades are spaced apart and are inclined whereby rotation of the impeller 28 induces flow of fluid in the flow path 7. Any suitable drive means can be used and, as shown, a shaft 31 is rotatably sleeved on the shaft 25 and is operably connected to the support 30. The shaft 31 is operably connected to power means for driving of the impeller. The drive means can be the motor 24 which would be operably connected to the shaft 31 by a gear reducing unit or preferably the shaft 31 is operably connected to a second motor 32 which preferably has a controllable speed for driving the impeller at a predetermined speed. The shaft 31 is rotatably mounted in a bearing arrangement 33 and is suitably sealed against leakage of fluid from the chamber 3. It is to be noted that more than one impeller 28 can be provided in the flow path 7 at spaced intervals along the length of the draft tube 6 to effect flow of fluid through the flow path 7. Alternately, it can be seen that the impeller 28 can be secured to the draft tube 6 which can in turn be rotated to effect pumping action of the flow inducing means 27.

Foam separating means 35 can be mounted in the chamber 3, if desired, to effect separation of the liquid phase from the gas phase of foam produced in the fermentation process. Although a foam fermentation process is described, non-foam fermentation processes can also be carried out in the apparatus. Any suitable type of foam separating means can be used and, as shown, a centrifugal type having discs 36 power driven by drive means 37 such as an electric motor whereby centrifugal force separates the liquid phase and gas phase with the gas escaping through a conduit (not shown) of the foam separating means 35. It is to be noted that a mechanical type of foam separating means, as shown, can be employed alone or a chemical defoaming agent can be used in place of or in conjunction with the mechanical foam separating means 35.

Fluid flow inducing means 39 can be provided to supplement the pumping action of the pump means 22 and the flow inducing means 27 to help improve circulation of the fluid medium in the chamber 3. As shown, an impeller-type of pump 40 is positioned adjacent the upper open end 21 of the draft tube 6 to help induce downward flow of fluid medium through the draft tube and to the pump means 22. The impeller 40 is operably connected to drive means which can be either the motor 32 or a separate motor which preferably is controllable in speed to control the operating speed of the impeller 40. Any suitable type of impeller or pump 40 can be used and, as shown, is of a type having a plurality of blades 41 secured to a shaft 42 which in turn is operably connected to suitable drive means such as the motor 37. Suitable heat exchange means are in heat transfer relation with the chamber 3 and, as shown, a heat exchanger 44 is mounted in the draft tube 6.

In operation, a suitable microorganism is injected into the chamber 3 along with fluid medium containing a carbonaceous material and other compounds and minerals necessary for the growth of the microorganisms. The apparatus 1 can be operated in a continuous manner or as a batch type but preferably is operated in a continuous manner wherein fluid medium is continually introduced into the vessel 2 and product is continually drawn off from the vessel 2. Oxygen or air is supplied through the oxygen supply 12. The pump means 22 and, if used, the impeller 40 induce downward flow of fluid medium through the draft tube 6 and out through the openings 23. The fluid medium then flows upwardly through the flow path 7 and foam is collected in the upper portion of the chamber 3. The foam separating means 35 break the foam into a liquid phase and a gas phase with the gas escaping through an exhaust (not shown) and the liquid portion falls downwardly through the chamber 3 for recirculation through the draft tube 6 and the flow path 7. The impeller 28 aids in upward flow of the fluid medium through the flow path 7 and preferably is operated at a speed sufficiently slow to prevent high shear pumping or breaking of the foam into gas and liquid phases. The pump means 22, impeller 28 and impeller 40 induce and maintain circulation in the chamber 3 and also aid in mixing of the fluid medium. Preferably, the heat exchanger 44 is provided to remove heat from the fluid medium which is produced by the fermentation.

It is to be understood that while I have illustrated and described certain forms of my invention, it is not to be limited to the specific form or arrangement of parts therein described and shown.

What is claimed and desired to be secured by Letters Patent is:

1. A fermentation apparatus including;
   a. a vessel with a chamber and having an interior surface, said vessel being adapted to contain a fluid;
   b. a draft tube mounted in the interior of said vessel and having opposite ends with flow openings adjacent each end, said draft tube being spaced from said interior surface defining a flow path therebetween;
   c. pump means in said vessel and positioned adjacent at least one of said draft tube ends for inducing flow of fluid through said draft tube;
   d. an impeller positioned between said draft tube and said interior surface; and
   e. means operably connected to said impeller for rotating same.

2. The fermentation apparatus as set forth in claim 1 wherein:
   a. said pump means includes a pump positioned adjacent each end of said draft tube.

3. The fermentation apparatus as set forth in claim 1 including:
   a. heat exchange means mounted in said vessel; and wherein
   b. said pump means includes a pump positioned adjacent a lower disposed end of said draft tube for pumping fluid through said draft tube and into said flow path.

4. A fermentation apparatus for the culturing of a microorganism by aerobic fermentation, said apparatus including:
   a. a vessel with a chamber therein and having an interior surface;
   b. a draft tube mounted in said vessel chamber and being spaced from said interior surface defining a first fluid flow path therebetween, said draft tube having opposite ends with a flow opening adjacent each said end, said draft tube defining a second fluid flow path;
   c. a first pump means positioned adjacent one of said ends and adapted to induce flow of fluid along said first and second flow paths and through said openings;
   d. an impeller positioned between said draft tube and said interior surface and being rotatable about an axis generally coaxial with an axis of said draft tube and adapted for inducing flow of fluid generally opposite to the direction of fluid flow through said draft tube; and e. power means operably connected to said first pump means and said impeller for driving same.

5. The fermentation apparatus as set forth in claim 4 including:
 a. a second pump means positioned at an end of said draft tube opposite said first pump means and being operably connected to second power means for driving thereby.

6. The ferementation apparatus as set forth in claim 4 wherein:
 a. said power means includes first and second motors, said first motor is operably connected to said impeller and said second motor is operably connected to said first pump means.

* * * * *